(12) United States Patent
Leibman

(10) Patent No.: US 10,568,610 B2
(45) Date of Patent: Feb. 25, 2020

(54) FUNNEL FOR URINE SAMPLING

(71) Applicant: Faith H. Leibman, Narberth, PA (US)

(72) Inventor: Faith H. Leibman, Narberth, PA (US)

( * ) Notice: Subject to any disclaimer, the term of this patent is extended or adjusted under 35 U.S.C. 154(b) by 239 days.

(21) Appl. No.: 15/612,160

(22) Filed: Jun. 2, 2017

(65) Prior Publication Data

US 2018/0344295 A1    Dec. 6, 2018

(51) Int. Cl.
*A61B 10/00* (2006.01)

(52) U.S. Cl.
CPC .................... *A61B 10/007* (2013.01)

(58) Field of Classification Search
CPC ....... A61B 10/007; A61B 5/451; A61B 5/453; A61B 5/455; A61B 5/4556
See application file for complete search history.

(56) References Cited

U.S. PATENT DOCUMENTS

| | | | |
|---|---|---|---|
| 3,583,388 A * | 6/1971 | Hovick | A61B 10/007 600/574 |
| 3,718,431 A * | 2/1973 | Wild | A61B 10/0038 4/144.1 |
| D227,413 S | 6/1973 | Sherin | |
| D265,586 S | 7/1982 | Sloan | |
| 4,421,511 A * | 12/1983 | Steer | A61F 5/455 4/144.3 |
| D290,880 S | 7/1987 | Blanton | |
| D296,496 S | 7/1988 | Kang | |
| 4,815,151 A * | 3/1989 | Ball | A61F 5/4556 4/144.1 |
| 5,129,892 A | 7/1992 | McCarthy | |
| 5,263,947 A * | 11/1993 | Kay | A61F 5/451 600/574 |
| 5,762,120 A | 6/1998 | Smith | |
| 6,151,721 A | 11/2000 | Whitfield | |
| D456,898 S | 5/2002 | Yang | |
| 6,434,757 B1 | 8/2002 | Filsouf | |
| 6,537,262 B2 | 3/2003 | Thompson | |
| D589,764 S | 4/2009 | Randolph | |
| D600,498 S | 9/2009 | Ma | |
| D606,373 S | 12/2009 | McCaffery | |
| D629,269 S | 12/2010 | Okamoto | |
| D640,904 S | 7/2011 | Wax | |
| D721,579 S | 1/2015 | Ott | |
| D733,199 S | 6/2015 | Kimmel | |
| D744,641 S | 12/2015 | Aiken | |
| D776,807 S | 1/2017 | Chacchia | |
| 2002/0179794 A1 | 12/2002 | Yang | |
| 2006/0111647 A1 | 5/2006 | Starling et al. | |
| 2007/0006368 A1 | 1/2007 | Key | |
| 2009/0124929 A1 | 5/2009 | Rossi-Pipitone et al. | |

FOREIGN PATENT DOCUMENTS

CN        203203835        9/2013

\* cited by examiner

*Primary Examiner* — Eric F Winakur
*Assistant Examiner* — Chu Chuan Liu
(74) *Attorney, Agent, or Firm* — Ballard Spahr LLP

(57) ABSTRACT

A funnel has a collar surrounding a flow axis. A surface, defined by lobes or a shell surrounds and faces the flow axis. The surface has an extended lateral shape afforded by different sized lobes, a trapezoidal or a rectangular perimeter. The funnel is removably attachable to a container.

8 Claims, 5 Drawing Sheets

US 10,568,610 B2

FUNNEL FOR URINE SAMPLING

FIELD OF THE INVENTION

The invention concerns funnels, for example, for taking urine samples.

BACKGROUND

Urine samples are taken routinely, for example, for drug testing, to detect diseases of the urinary system, metabolic diseases such as diabetes or liver disease and other medical procedures. Women face challenges distinct from men in the collection of urine samples because unlike men, they have less control over the direction of their urine stream. Of particular concern is the capture of lateral urine spray in the direction of the coronal body plane. There is clearly a need for a device which addresses the challenges faced by women in this regard.

SUMMARY

The invention concerns a funnel removably attachable to a container having an open end. In one example embodiment the funnel comprises a collar surrounding a bore defining a coaxial flow axis. The collar is adapted to receive the open end of the container. A plurality of lobes are attached to the collar. The lobes define a surface surrounding and facing the flow axis. A first and a second one of the lobes are positioned on a first side of the flow axis. A third and a fourth one of the lobes are positioned in opposition to the first and second lobes. The third lobe is larger than both the first lobe and the second lobe, and the fourth lobe being larger than both the first lobe and the second lobe.

In an example embodiment, a fifth one of the lobes may be positioned between the third and the fourth lobes. By way of example, each of the lobes may have a curved perimeter. In an example embodiment, each of the lobes has a curvature extending circumferentially about the flow axis. Each of the lobes may be joined to an adjacent lobe along an apex extending from the collar to a perimeter of the lobes. In another example embodiment, each of the lobes has a curvature extending between a perimeter of each the lobe and the collar.

In an example funnel according to the invention, screw threads may be positioned on a surface of the collar facing the flow axis. Further by way of example, a handle projecting away from the flow axis, is positioned adjacent to the third and fourth lobes. In an example embodiment the handle may comprise a tab oriented transversely to the flow axis. Further by way of example, the handle may project away from the flow axis. In another example the handle is attached to the fifth lobe.

In an example embodiment, the third lobe has a larger surface area than either the first or second lobes. In a further example, the fourth lobe has a larger surface area than either the first or second lobes. Additionally by way of example, the third lobe subtends a larger angle about the flow axis than either the first or second lobes. Again by way of example, the fourth lobe subtends a larger angle about the flow axis than either the first or second lobes. In an example embodiment, a perimeter of the third lobe, at its furthest extent, is further from the flow axis than a perimeter of either the first or second lobes at their respective furthest extents. Further by way of example, a perimeter of the fourth lobe, at its furthest extent, is further from the flow axis than a perimeter of either the first or second lobes at their respective furthest extents.

The invention also encompasses a kit, comprising, in combination, the container and the funnel.

In another example embodiment of a funnel removably attachable to a container, the funnel comprises a collar surrounding a bore defining a coaxial flow axis. The collar is adapted to receive the open end of the container. A shell is attached to the collar. The shell defines a surface surrounding and facing the flow axis. The shell has a trapezoidal perimeter when viewed along the flow axis. In an example embodiment, the trapezoidal perimeter may have rounded corners. By way of example, the shell has a curvature extending circumferentially about the flow axis. Further by way of example, the shell has a curvature extending between the perimeter and the collar. In an example embodiment the funnel further comprises a handle attached to the shell. The handle projects away from the flow axis in an example embodiment. In a particular example, the handle comprises a tab oriented transversely to the flow axis.

In an example funnel according to the invention, the perimeter comprises a side having a greater length than all other sides comprising the perimeter. By way of example the handle may be attached to the shell adjacent to the side having the greatest length. In an example embodiment, comprising screw threads are positioned on a surface of the collar facing the flow axis. The invention also encompasses a kit, comprising, in combination, the container and the funnel.

In another example embodiment of a funnel removably attachable to a container having an open end, the funnel comprises a collar surrounding a bore defining a coaxial flow axis. The collar is adapted to receive the open end of the container. A shell is attached to the collar. The shell defines a surface surrounding and facing the flow axis. The shell has a rectangular perimeter when viewed along the flow axis.

By way of example, the rectangular perimeter may have rounded corners. In an example embodiment, the shell has a curvature extending circumferentially about the flow axis. Further by way of example, the shell has a curvature extending between the perimeter and the collar.

In an example embodiment, a handle is attached to the shell, the handle projecting away from the flow axis. In an example embodiment, the handle comprises a tab oriented transversely to the flow axis.

By way of example, the perimeter comprises first and second sides oppositely disposed from one another. The first and second sides have a greater length than a third and a fourth side also comprising the perimeter. In an example embodiment, the handle is attached to the shell adjacent to the first side. An example funnel embodiment further comprises screw threads positioned on a surface of the collar facing the flow axis.

The invention also encompasses a kit, comprising, in combination, the container and the funnel.

In another example embodiment of a funnel removably attachable to a container having an open end, the funnel comprises a collar surrounding a bore defining a coaxial flow axis. The collar is adapted to receive the open end of the container a plurality of lobes are attached to the collar. The lobes define a surface surrounding and facing the flow axis. A first and a second one of the lobes are positioned on one side of the flow axis. A third and a fourth one of the lobes are positioned on an opposite side of the flow axis. The span of the lobes, measured along a first line oriented perpendicular to the flow axis, is greater than the span of the lobes measured along a second line perpendicular to the first line and the flow axis in this example embodiment.

In an example embodiment, each of the lobes has a curved perimeter. Further by way of example, each of the lobes has a curvature extending circumferentially about the flow axis. Additionally by way of example, each of the lobes has a curvature extending between a perimeter of each the lobe and the collar. An example embodiment further comprises screw threads positioned on a surface of the collar facing the flow axis. By way of example, a a handle may be attached to at least one of the lobes, the handle being positioned along the greater span of the lobes. In an example embodiment, the handle comprises a tab oriented transversely to the flow axis and projecting away therefrom. The invention further encompasses a kit, comprising, in combination, the container and the funnel in an example.

DETAILED DESCRIPTION

Figure 1:
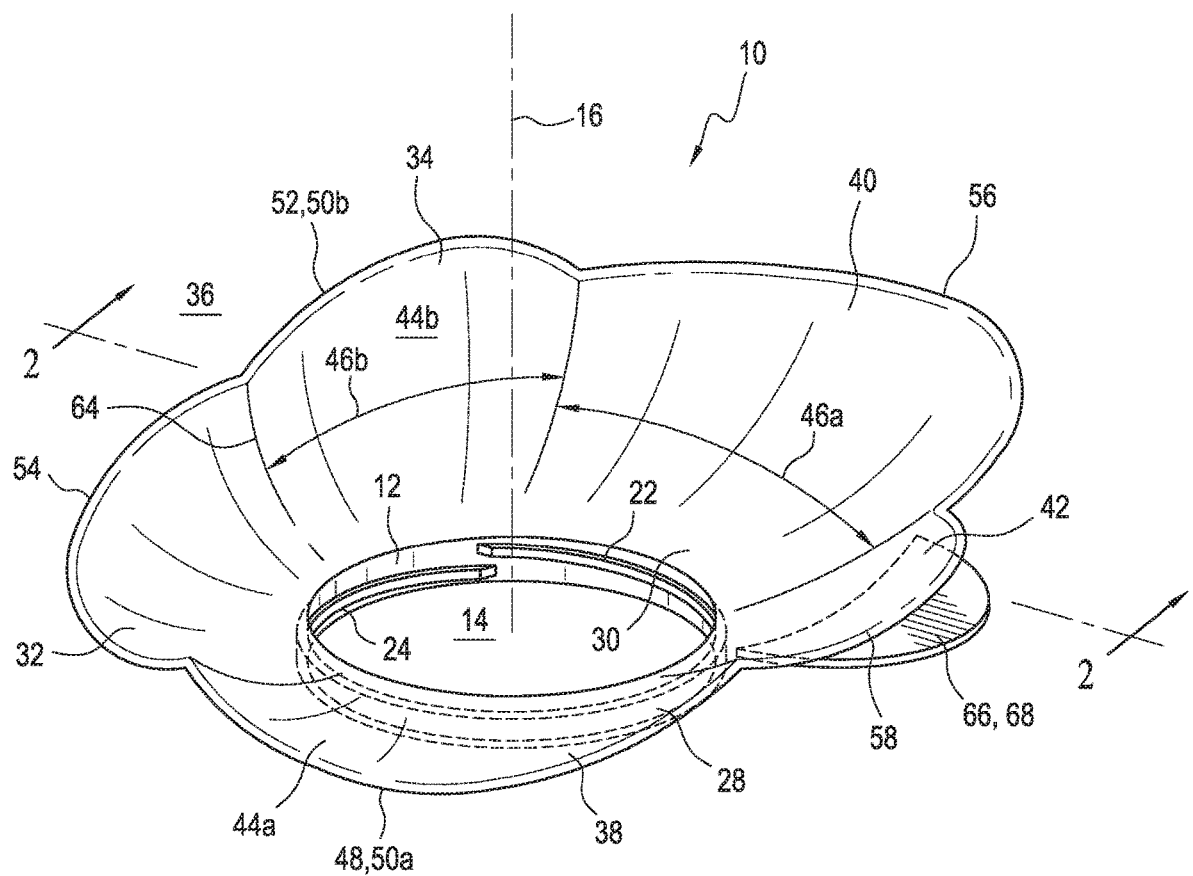
FIG. 1 is an isometric view of an example embodiment of a funnel according to the invention.
Figure 2:
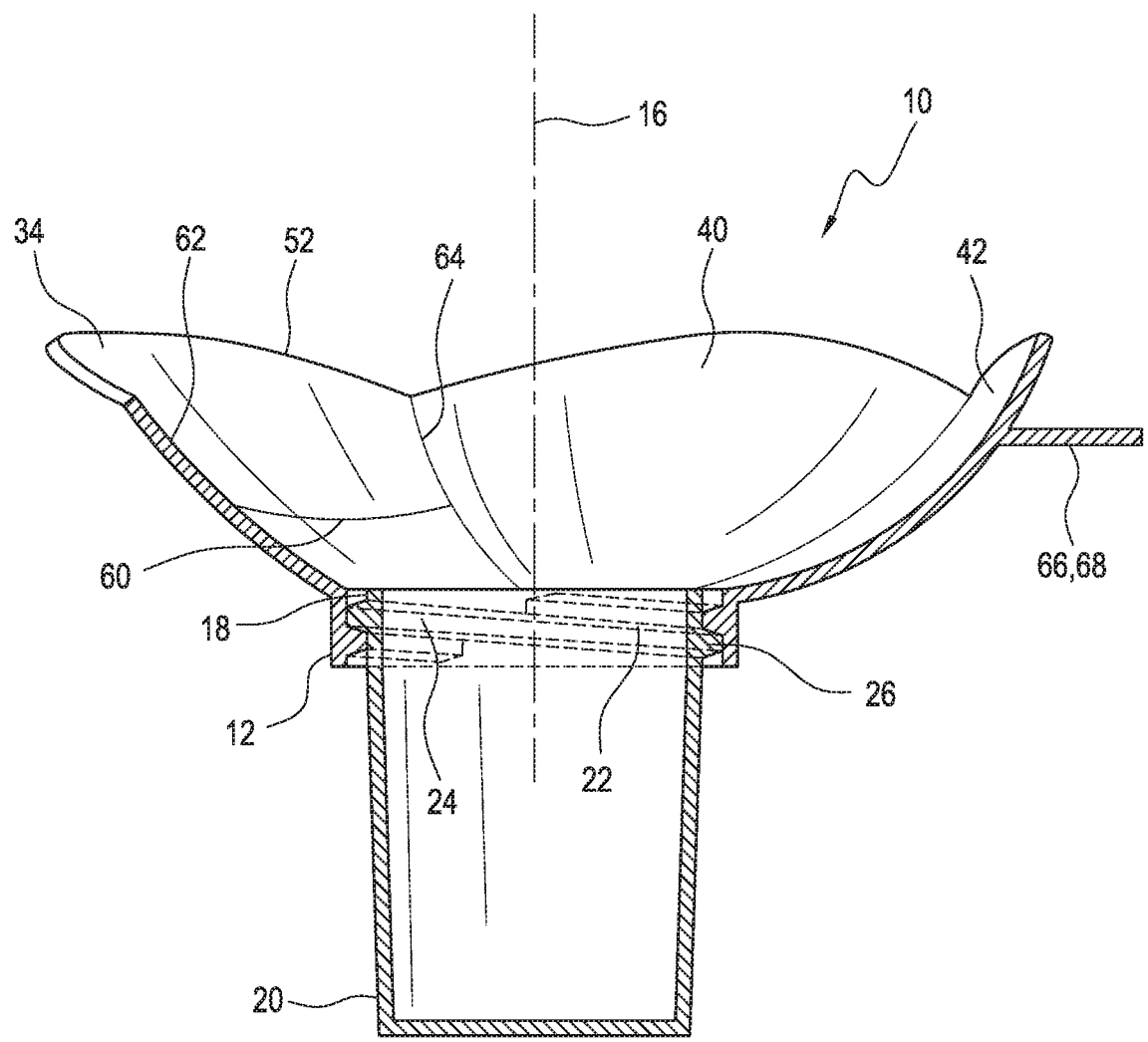
FIG. 2 is a sectional view taken at line 2-2 of FIG. 1 and showing an example combination funnel and container.

FIG. 1 shows an example embodiment of a funnel 10 according to the invention. Funnel 10 comprises a collar 12 surrounding a bore 14. Bore 14 defines a flow axis 16 arranged coaxially with the bore. As shown in FIG. 2, collar 12 is adapted to receive the open end 18 of a container 20, for example, a container for a urine sample. To that end screw threads 22 are positioned on a surface 24 of collar 12 which faces the flow axis 16. Screw threads 22 engage compatible screw threads 26 surrounding the open end 18 of the container 20. In another embodiment collar 12 receives open end 18 of container 20 in a friction fit. With the use of screw threads or a friction fit, the funnel 10 is removably attachable to the container 20.

As shown in FIG. 1, a plurality of lobes 28 are attached to the collar 12. Lobes 28 define a surface 30 which surrounds and faces the flow axis 16. A first and a second lobe, 32 and 34, are positioned on a first side 36 of the flow axis 16. Third and fourth lobes 38 and 40 are positioned in opposition to the first and second lobes 32 and 34. A fifth lobe 42 may be positioned between the third and fourth lobes 38 and 40. The third lobe 38 is larger than both the first lobe 32 and the second lobe 34. The fourth lobe 40 is larger than both the first lobe 32 and the second lobe 34. The term "larger" in this context means that the larger lobe, for example, lobe 38 and 40, has at least one or more of the following characteristics when compared with the smaller lobes, for example, lobes 32 and 34: the larger lobe has a larger surface area 44a than the surface area 44b of the smaller lobe; the larger lobe subtends a larger angle 46a about the flow axis 16 than the angle 46b subtended by the smaller lobe; and/or the perimeter 48 of the larger lobe, at its furthest extent 50a from the flow axis 16, is further from the flow axis 16 than the perimeter 52 of the smaller lobe at its furthest extent, 50b.

The respective perimeters 48, 52, 54, 56, 58 of each of the lobes 38, 34, 32, 40 and 42 may be curved, as shown by way of example. Further in the illustrated embodiment as shown for lobe 34 in FIG. 2, each lobe 32, 34, 38, 40 and 42 may have a compound curvature, i.e., each lobe may have a curvature 60 extending circumferentially about the flow axis 16, and each lobe may have a curvature 62 extending from a perimeter (perimeter 52 for lobe 34) of the lobe to the collar 12. The curvatures 60 and 62 of each lobe result in adjacent lobes joining to one another along apex lines 64 extending between the collar 12 to a lobe perimeter.

FIGS. 1 and 2 further illustrate a handle 66, which may be attached adjacent to the third and fourth lobes 38, and 40, for example to the fifth lobe 42 when present. Handle 66 projects away from the flow axis 16. In this example embodiment the handle 66 comprises a tab 68 oriented transversely to the flow axis.

Figure 3:
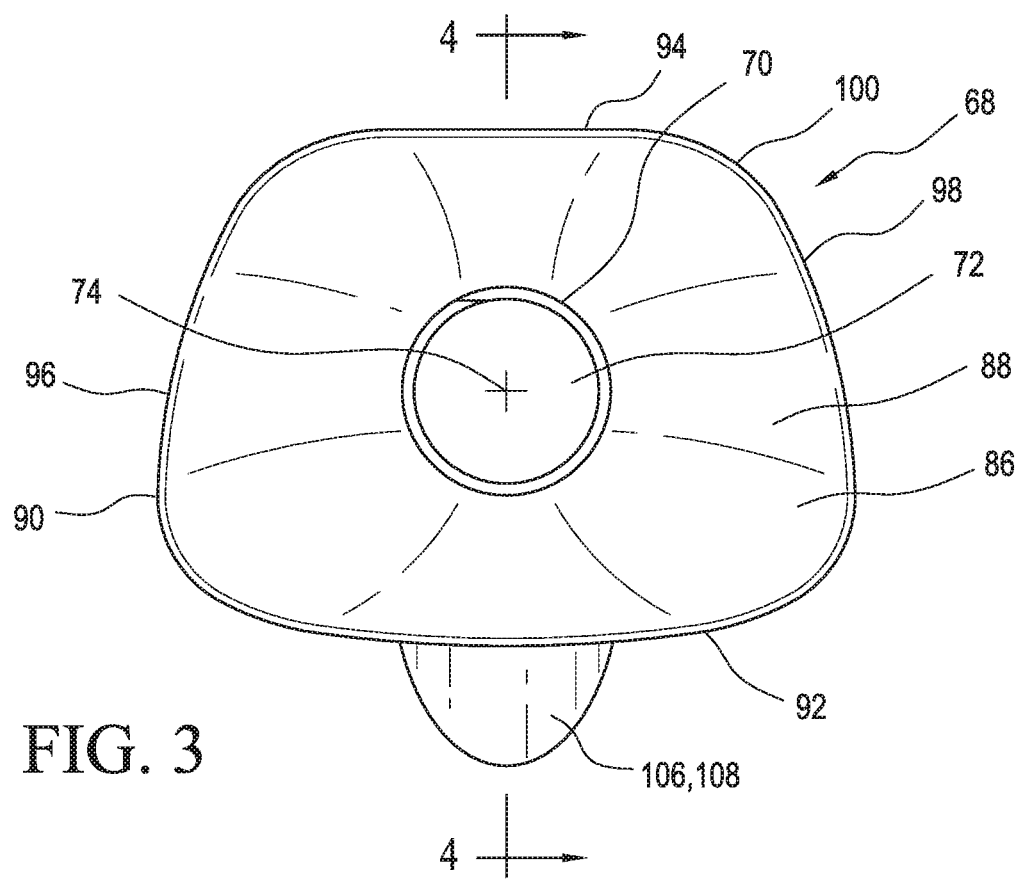
FIG. 3 is a top view of another example embodiment of a funnel according to the invention.
Figure 4:
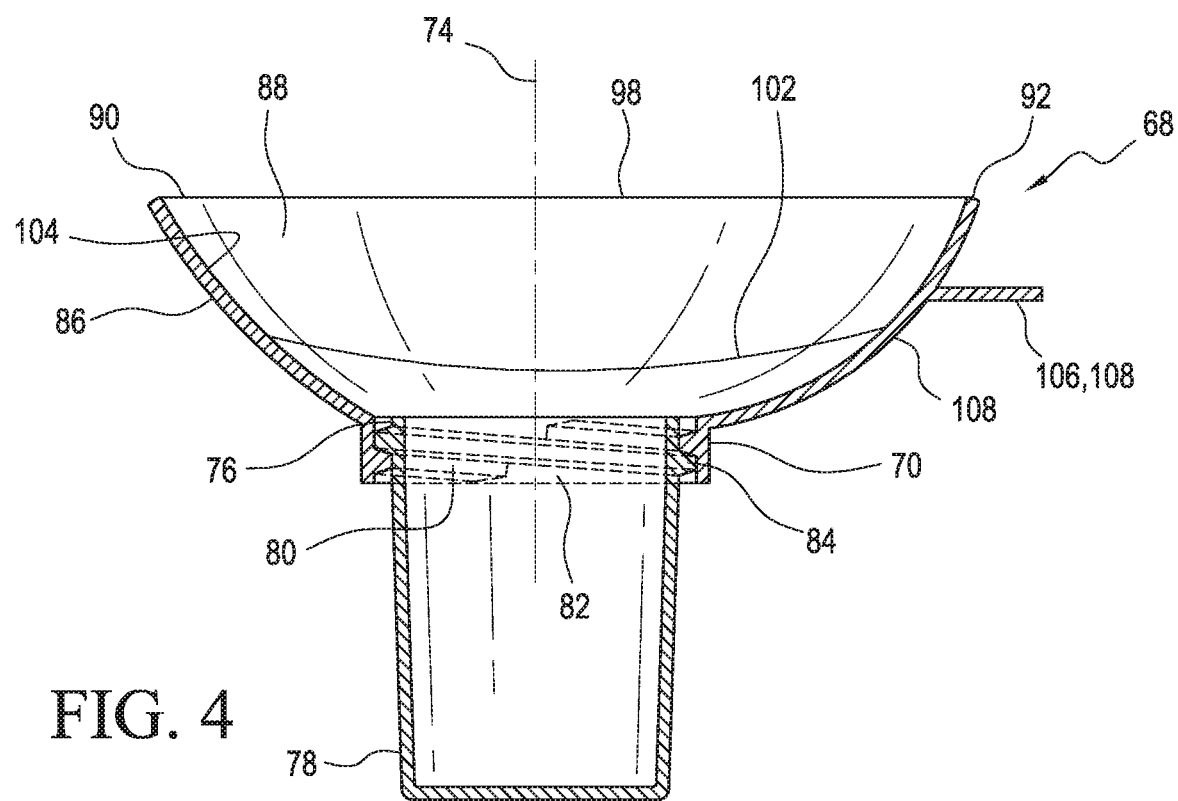
FIG. 4 is a sectional view taken at line 4-4 of FIG. 3 showing an example combination funnel and container.

FIGS. 3 and 4 illustrate another example embodiment of a funnel 68 according to the invention. Funnel 68 comprises a collar 70 which surrounds a bore 72. Bore 72 defines a flow axis 74 arranged coaxially with the bore. Collar 70 is adapted to receive an open end 76 of a container 78, for example, a container for a urine sample. As shown in FIG. 4, funnel 68 is removably attachable to the container 78. To that end screw threads 80 are positioned on a surface 82 of collar 70 which faces the flow axis 74. Screw threads 80 engage compatible screw threads 84 surrounding the open end 76 of the container 78. In another embodiment, collar 70 receives open end 76 of container 78 in a friction fit. With the use of screw threads or a friction fit, the funnel 68 is removably attachable to the container 78.

As shown in FIG. 3, a shell 86 is attached to collar 70. Shell 86 defines a surface 88 which surrounds and faces the flow axis 74 (see also FIG. 4). When viewed along the flow axis 74 (FIG. 3) the shell 86 has a trapezoidal perimeter 90. The term "trapezoidal" as used herein means the perimeter has a base portion 92 which is wider than a top portion 94, the base portion being connected to the top portion by side portions 96 and 98. In this example the side portions 96 and 98 meet the top and base portions 94 and 92 at rounded corners 100. The various portions of the perimeter are furthermore curved for reasons of comfort to the user, but other corner configurations, such as polygonal or angled are also feasible.

As shown in FIG. 4, the shell 86 may have compound curvature, i.e., the shell may have a curvature 102 extending circumferentially about the flow axis 16, and a curvature 104 extending from the perimeter 90 to the collar 70. FIGS. 3 and 4 further illustrate a handle 106, which may be attached to the shell 86 adjacent to the base portion 92 of the perimeter 90, the base portion 92 being the side of the perimeter 90 having a greater length than all of the other sides. Handle 106 is attached to a surface 108 of shell 86 opposite to surface 88 and projects away from the flow axis 74. In this example embodiment the handle 106 comprises a tab 108 oriented transversely to the flow axis.

Figure 5:
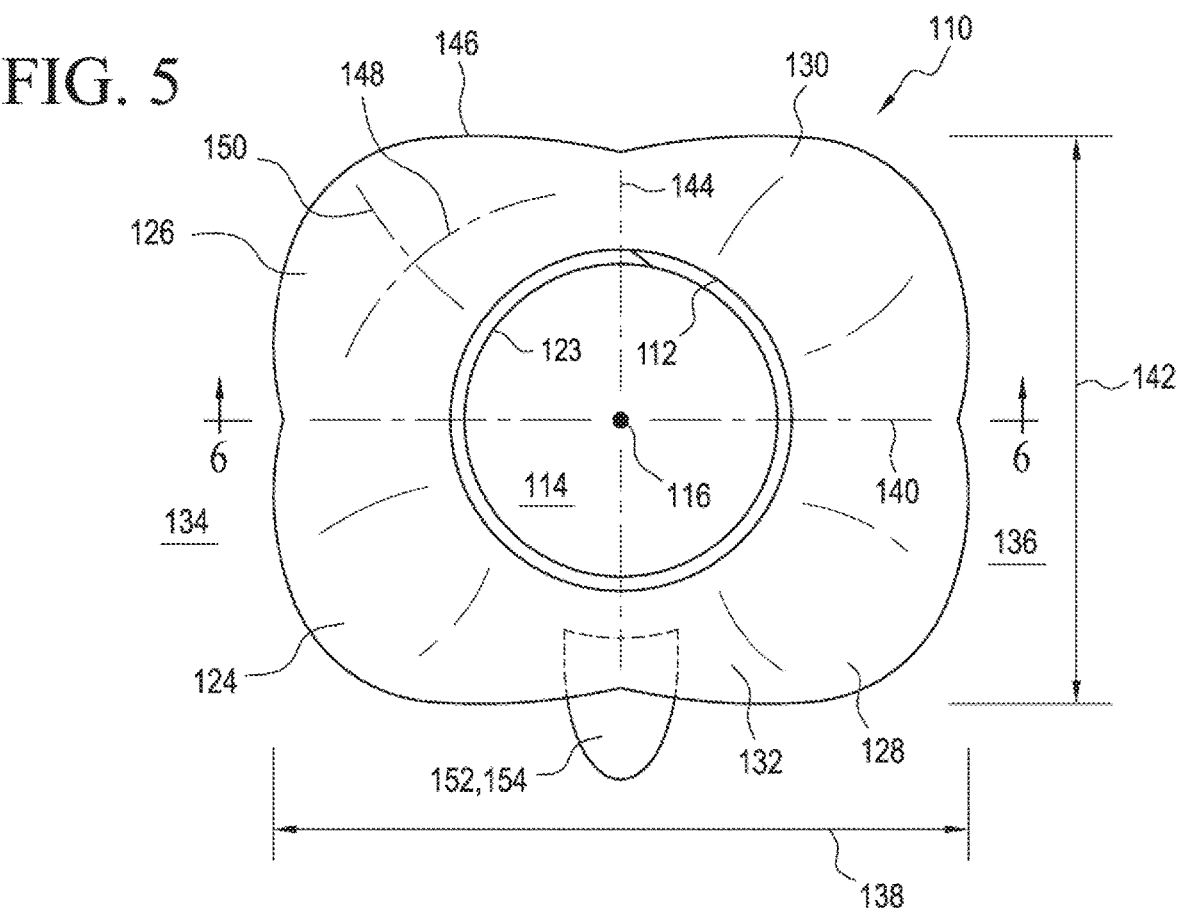
FIG. 5 is a top view of another example embodiment of a funnel according to the invention.
Figure 6:
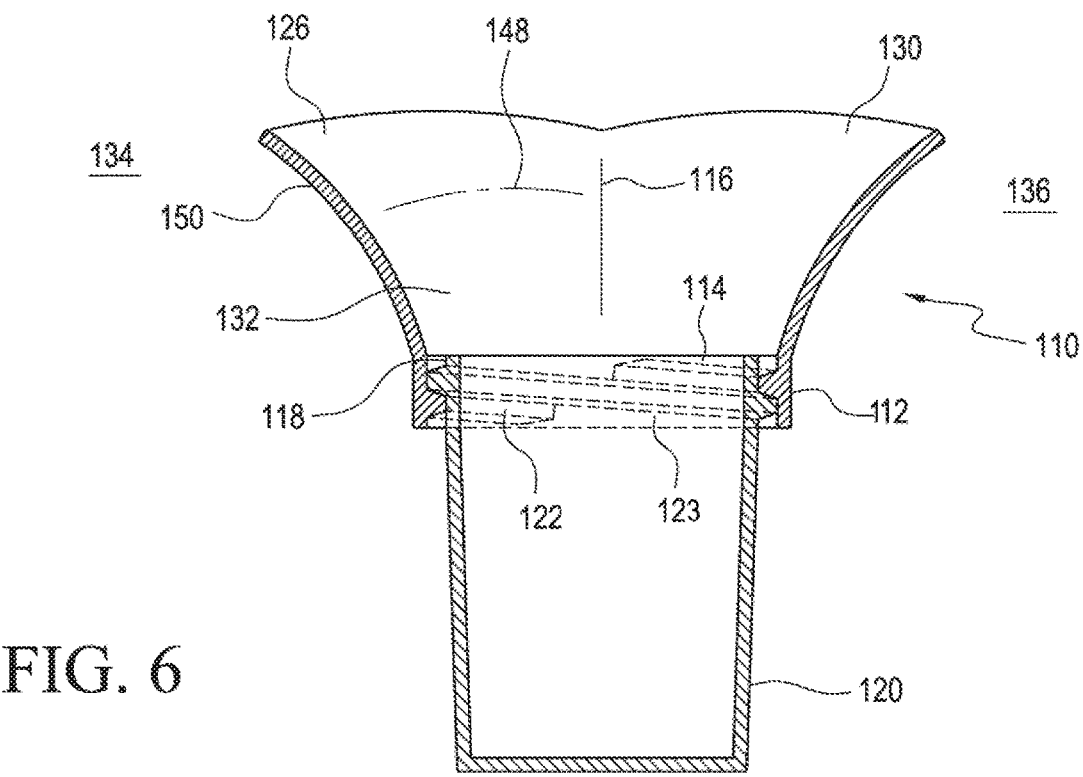
FIG. 6 is a sectional view taken at line 6-6 of FIG. 6 showing an example combination funnel and container.

FIGS. 5 and 6 show another example embodiment of a funnel 110 according to the invention. Funnel 110 comprises a collar 112 surrounding a bore 114 which defines a coaxial flow axis 116. Collar 112 is adapted to receive the open end 118 of a container 120. The attachment between the container 120 and the funnel 110 may be by friction between the collar and the container, or by screw threads 122 positioned on a surface 123 of the collar that faces the flow axis 116, the screw threads engaging compatible screw threads surrounding the open end 118.

A plurality of lobes, in this example four lobes 124, 126, 128 and 130, are attached to the collar 112. The lobes define a surface 132 which surrounds and faces the flow axis 116. First and second lobes 124 and 126 are positioned on one side 134 of the flow axis 116, the third and fourth lobes 128 and 130 are positioned on the opposite side 136 of the flow axis. In this example embodiment, the span 138 of the lobes 124, 126, 128 and 130, measured along a first line 140 oriented perpendicular to the flow axis 116 is greater than the span of the lobes 142 measured along a second line 144 oriented perpendicular to both the first line 140 and the flow axis 116.

Each lobe 124, 126, 128 and 130 may have a curved perimeter 146, and each lobe may also have a compound curvature, i.e., each lobe may have a curvature 148 extending circumferentially about the flow axis 16, and each lobe may have a curvature 150 extending from a perimeter 146 of the lobe to the collar 112.

As shown in FIG. 5 a handle 152 may be attached to at least one of the lobes. Handle 152 is positioned along the side of the funnel 110 having the greater lobe span 138. In this example embodiment the handle 152 comprises a tab 154 oriented transversely to the flow axis 116 and projecting away therefrom.

Figure 7:
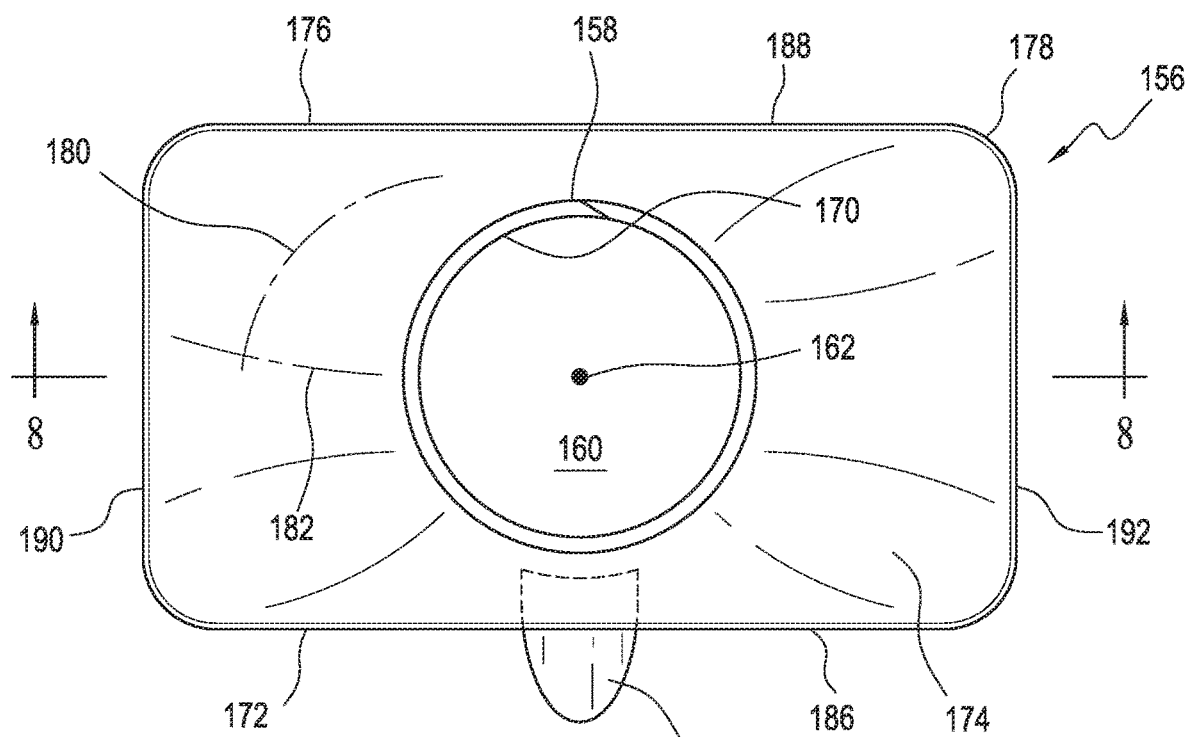
FIG. 7 is a top view of another example embodiment of a funnel according to the invention.
Figure 8:
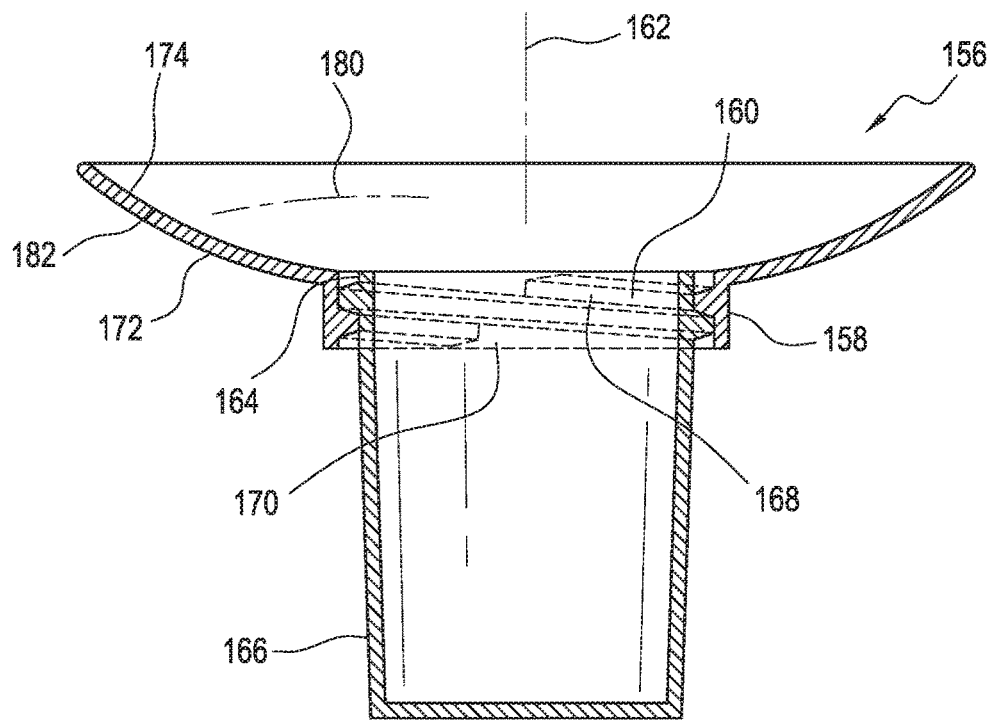
FIG. 8 is a sectional view taken at line 8-8 of FIG. 7 showing an example combination funnel and container.

FIGS. 7 and 8 illustrate another example embodiment of a funnel 156. Funnel 156 comprises a collar 158 surrounding a bore 160 which defines a coaxial flow axis 162. Collar 158 is adapted to receive the open end 164 of a container 166. The attachment between the container 166 and the funnel 156 may be by friction between the collar and the container, or by screw threads 168 positioned on a surface 170 of the collar that faces the flow axis 162, the screw threads engaging compatible screw threads surrounding the open end 164.

A shell 172 is attached to the collar 158. Shell 172 defines a surface 174 surrounding and facing the flow axis 162. Shell 172 has a rectangular perimeter 176 when viewed along the flow axis 162 as shown in FIG. 7.

The rectangular perimeter may have rounded corners 178 and may also have a compound curvature, i.e., the shell 172 may have a curvature 180 extending circumferentially about the flow axis 162, as well as a curvature 182 extending from the perimeter 176 to the collar 112.

As shown in FIG. 7 a handle 184 may be attached to the shell 172. As shell 172 has a rectangular perimeter 176, first and second sides 186 and 188, oppositely disposed from one another, have a greater length than third and fourth sides 190 and 192. Handle 184 is positioned along the side of the funnel 156 having the greater length, for example the first side 186. Further in this example embodiment, the handle 184 comprises a tab 194 oriented transversely to the flow axis 162 and projecting away therefrom.

Example funnels 10 and 68, 110 and 156 according to the invention are advantageously made of polymers such as polypropylene. Such materials permit an inexpensive and light weight design appropriate for one time use and disposal as is customary in medical sampling and testing procedures. In particular, when the funnels are made of polypropylene it permits them to be folded into a smaller size for economical packaging with a urine sample container to form a kit comprising the combination of a funnel and container.

The advantage of both the lobed design of funnels 10 and 110 the trapezoidal design of funnel 68 and the rectangular design of funnel 156 resides in their laterally extended shape which is expected to better capture lateral spray of a urine stream from the female urethra. In use, the handle 66 in funnel 10 is held between the thumb and index finger, the funnel is positioned between the legs of the user and the surface 24 is positioned beneath the urethra. When held in this manner the first and second lobes 32 and 34 face the posterior and the laterally extended shape of the funnel 10 afforded by the third, fourth and fifth lobes 38, 40 and 42 aligns appropriately to effectively capture lateral spray. Funnels 68, 110 and 156 are used in a similar manner. When the handle 106 of funnel 68 is held the top (narrower) portion 94 of the perimeter 90 faces the posterior and the laterally extended shape afforded by the (wider) base portion 92 of the perimeter 90 aligns appropriately to permit surface 88 of shell 86 to effectively capture lateral spray in its position beneath the urethra. Alternatively, in the absence of a handle, the lower surface 108 of the shell 86 may be cupped by the fingers of the user to hold the funnel 68 in position. Funnels 10, 110 and 156 may also be held in this manner, the fingers contacting the surface opposite to surface 30, 132 or 170.

What is claimed is:

1. A funnel removably attachable to a container having an open end, said funnel comprising:
   a collar surrounding a bore defining a coaxial flow axis, said collar adapted to receive said open end of said container;
   a plurality of lobes attached to said collar, said lobes defining a surface surrounding and facing said flow axis;
   a first and a second one of said lobes being positioned on one side of a first line, said first line oriented perpendicular to and intersecting said flow axis, a third and a fourth one of said lobes being positioned on an opposite side of said first line, the span of said lobes measured along said first line being greater than the span of said lobes measured along a second line perpendicular to and intersecting both said first line and said flow axis, wherein said first and said third one of said lobes are positioned on one side of said second line and said second and said fourth one of said lobes are positioned on an opposite side of said second line.

2. The funnel according to claim 1, wherein each of said lobes has a curved perimeter.

3. The funnel according to claim 1, wherein each of said lobes has a curvature extending circumferentially about said flow axis.

4. The funnel according to claim 1, wherein each of said lobes has a curvature extending between a perimeter of each said lobe and said collar.

5. The funnel according to claim 1, further comprising screw threads positioned on a surface of said collar facing said flow axis.

6. The funnel according to claim 1, further comprising a handle attached to at least one of said lobes, said handle being positioned along said greater span of said lobes.

7. The funnel according to claim 6, wherein said handle comprises a tab oriented transversely to said flow axis and projecting away therefrom.

8. A kit, comprising, in combination, said container and said funnel according to claim 1.

* * * * *